(12) United States Patent
Sivavec et al.

(10) Patent No.: US 6,485,688 B1
(45) Date of Patent: Nov. 26, 2002

(54) ON-LINE SPARGING SAMPLING AND MONITORING SYSTEMS AND METHODS

(75) Inventors: Timothy Mark Sivavec, Clifton Park, NY (US); Sunita Singh Baghel, Rensselaer, NY (US); Angelo Anthony Bracco, Albany, NY (US); Don Royall Houston, Rensselaer, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/556,288

(22) Filed: Apr. 24, 2000

(51) Int. Cl.$^7$ ................................................. G01N 7/00
(52) U.S. Cl. ........................ 422/83; 422/68.1; 73/23.2; 73/19.1
(58) Field of Search .................... 700/273, 83; 73/19.1, 73/53.01, 61.43; 436/121, 181; 714/37; 95/245, 141; 422/99, 68.1, 83; 210/703; 261/121.1

(56) References Cited

U.S. PATENT DOCUMENTS 3,550,917 A * 12/1970 Cochran .................. 261/121.1

(List continued on next page.)

OTHER PUBLICATIONS

Chemical Engineering Progress, "How Do New Process Analyzers Measure Up?", Podkulski, Daniel E., Chevron Products Co., pp. 33–46 (Oct. 1997).

Environmental Science & Technology, "Volatilization of Chemicals From Tap Water to Indoor Air From Contaminated Water Used for Showering", Moya, Jacqueline, Howard–Reed, Cynthia and Corsi, Richard L., vol. 33, No. 14, pp. 2321–2327 (1999).

Application Note, "Use of GC Analyzer With Continuous Sparger for Monitoring Polar and Nonpolar Species", Driscoll, John N., pp. 16 and 18 (Dec. 1998).

Primary Examiner—Jill Warden
Assistant Examiner—Brian Sines
(74) Attorney, Agent, or Firm—Noreen C. Johnson; Christian C. Cabou

(57) ABSTRACT

An on-line sparging sampling system and method sparges polar and non-polar volatile organic compounds from aqueous discharge. The system comprises a network of tubular members that are interconnected to each other to define a fluid passage, in which the network of tubular members comprises an inlet for influent aqueous discharge into the network of tubular members and an outlet for discharge of aqueous discharge from the on-line sparging sampling and monitoring system; a sparger disposed in the network of tubular members, in which the sparger is disposed between the inlet and the outlet of the aqueous discharge so that aqueous discharge flows by the sparger, the sparger providing inert non-reactive gas to the on-line sparging sampling and monitoring system; and at least one analytic device connected to the on-line sparging sampling and monitoring system for analyzing volatile organic compounds in the aqueous discharge. The aqueous discharge forms an aqueous discharge portion and a headspace during flow through the network of tubular members. The sparger provides the inert non-reactive gas to flow through the aqueous discharge portion. The inert non-reactive gas partitions volatile organic compounds from the aqueous discharge portion to the headspace. Thus, polar and non-polar volatile organic compounds can be analyzed by the at least one analytic device.

52 Claims, 6 Drawing Sheets

U.S. PATENT DOCUMENTS

| | | | | |
|---|---|---|---|---|
| 5,080,868 A | * | 1/1992 | Elgas | 422/99 |
| 5,122,166 A | * | 6/1992 | Hyrcyk et al. | 95/141 |
| 5,127,259 A | * | 7/1992 | Kahl et al. | 73/19.1 |
| 5,421,194 A | * | 6/1995 | Doyle et al. | 73/53.01 |
| 5,531,904 A | * | 7/1996 | Grisham et al. | 210/703 |
| 5,646,336 A | * | 7/1997 | Thompson et al. | 73/61.43 |
| 5,693,538 A | * | 12/1997 | Capuano et al. | 436/181 |
| 5,981,289 A | * | 11/1999 | Wright et al. | 436/121 |
| 6,123,750 A | * | 9/2000 | Espinal | 95/245 |
| 6,195,591 B1 | * | 2/2001 | Nixon et al. | 700/83 |
| 6,298,454 B1 | * | 10/2001 | Schleiss et al. | 714/37 |

* cited by examiner

ON-LINE SPARGING SAMPLING AND MONITORING SYSTEMS AND METHODS

BACKGROUND OF THE INVENTION

The invention relates to sampling and monitoring systems and methods. In particular, the invention relates to on-line sparging sampling and monitoring systems and methods.

Typically, a sampling system is used to monitor manufacturing processes, in which the sampling system may include analyzing capabilities. The sampling system should obtain a representative sample with minimal operations and time. While such sampling systems have been used in industry, these sampling systems may experience analytical problems, some of which may be attributed to sampling system features and mechanics.

Manufacturing processes may produce by-products, which need monitoring, such as by sampling and analyzing. A manufacturing process may produce volatile organic compound (VOCs) by-products at a process discharge, such as, but not limited to, an aqueous discharge. Typically, VOCs can comprise mixtures of polar and non-polar hydrocarbons. VOCs can pose analytical problems for conventional monitoring and sampling systems. Polar and non-polar hydrocarbons generally require two different and distinct processes for sampling from an aqueous discharge. Non-polar VOCs, such as, but not limited to, benzene, toluene, and aliphatic hydrocarbons including hexane, are generally sampled with a purge-and-trap method and analyzed by gas chromatography (gc). However, polar VOCs, including but not limited to acetone, methanol, and other alcohols, are typically sampled by sparging or dynamic headspace sampling and analyzed by gas chromatography. Alternatively, polar VOCs can be sampled by direct injection gas chromatography (gc).

If a monitoring system requires collection of samples (often known as "grab samples"), time delays between the actual sampling operation and the analyzing of the samples often occur. These time delays may be so long that the value of a sample is diminished because the by-product sample may not be reflective of actual and real-time by-products. Thus, the time delay is undesirable.

Further, the aqueous discharge being monitored may often contain sediment and particulates. Conduits in conventional sampling systems may be configured too narrowly and be constricted so that fouling and blockage by sediments or particulates often occurs and interrupts monitoring. Thus, filtering of influent aqueous discharge is needed. The filters in conventional monitoring systems need to be cleaned and replaced, which is both inefficient and un-economical.

Improvements and advancements have been proposed for sampling systems. For example, advancements have been made in on-line sampling systems including, but not limited to, sample validation techniques, modular designs, new sampling system materials, probe enhancements including fiber-optic probes, enhanced membrane technology, and re-designed valves and filters. These on-line sampling system advancements have been useful. However, if these on-line sampling system advancements are applied to old sampling system technology, analytical problems may still arise since the sampling system is limited by the old sampling system technology of the on-line sampling system.

Therefore, improvements in on-line sampling technology are needed to keep up with current process analyzer technology. Further, a sampling system that is able to sample and monitor polar and non-polar VOCs is needed. Furthermore, a sampling system that is able to sample and monitor without delays, which are associated with some conventional sampling systems, is needed

SUMMARY OF THE INVENTION

An aspect of the invention provides on-line sparging sampling system and method that sparges polar and non-polar volatile organic compounds from aqueous discharge. The system comprises a network of tubular members that are interconnected to each other to define a fluid passage, in which the network of tubular members comprises an inlet for influent aqueous discharge into the network of tubular members and an outlet for discharge of aqueous discharge from the on-line sparging sampling and monitoring system; a sparger disposed in the network of tubular members, in which the sparger is disposed between the inlet and the outlet of the aqueous discharge so that aqueous discharge flows by the sparger, the sparger providing inert non-reactive gas to the on-line sparging sampling and monitoring system; and at least one analytic device connected to the on-line sparging sampling and monitoring system for analyzing volatile organic compounds in the aqueous discharge. The aqueous discharge forms an aqueous discharge portion and a headspace during flow through the network of tubular members. The sparger provides the inert non-reactive gas to flow through the aqueous discharge portion. The inert non-reactive gas partitions volatile organic compounds from the aqueous discharge portion to the headspace. Thus, polar and non-polar volatile organic compounds can be analyzed by the at least one analytic device.

Another aspect of the invention sets forth a method for on-line sparge sampling by sparging polar and non-polar volatile organic compounds from aqueous discharge using an on-line sparging sampling and monitoring system. The method comprises providing a network of tubular members that are interconnected to each other to define a fluid passage; providing an inlet for influent aqueous discharge into the network of tubular members and an outlet for discharge from the on-line sparging sampling and monitoring system; disposing a sparger between the inlet and the outlet of the aqueous discharge; flowing aqueous discharge by the sparger; providing inert non-reactive gas from the sparger to flow through the aqueous discharge in the on-line sparging sampling and monitoring system; flowing the inert gas through the aqueous discharge; forming a aqueous discharge portion and a headspace in the network of tubular members during aqueous discharge flow through the network of tubular members; monitoring and analyzing the sparged aqueous discharge in the on-line sparging sampling and monitoring system for volatile organic compounds using at least one analytic device; and partitioning volatile organic compounds from the aqueous discharge portion to the headspace so that polar and non-polar volatile organic compounds can be analyzed.

These and other aspects, advantages and salient features of the invention will become apparent from the following detailed description, which, when taken in conjunction with the annexed drawings, where like parts are designated by like reference characters throughout the drawings, disclose embodiments of the invention.

DESCRIPTION OF THE INVENTION

An on-line sparging (dynamic headspace) sampling and monitoring system, as embodied by the invention, sparges both non-polar and polar volatile organic compounds (VOCs) from an aqueous stream. The on-line sparging sampling and monitoring system comprises features that provide robustness to the sampling system. The term robustness means that a long-term performance of the system occurs with little or no upkeep or maintenance, and is not typically prone to failure. The on-line sparging sampling and monitoring system features also reduce maintenance time and costs typically associated with conventional sampling systems. The on-line sparging sampling and monitoring system, as embodied by the invention, is configured to avoid sample conditioning, such as filtering, to remove particulates and sediments. These particulates and sediments were believed to foul and lead to sampling and analyzer systems malfunctions and repair or replacement of the filters.

Figure 1:
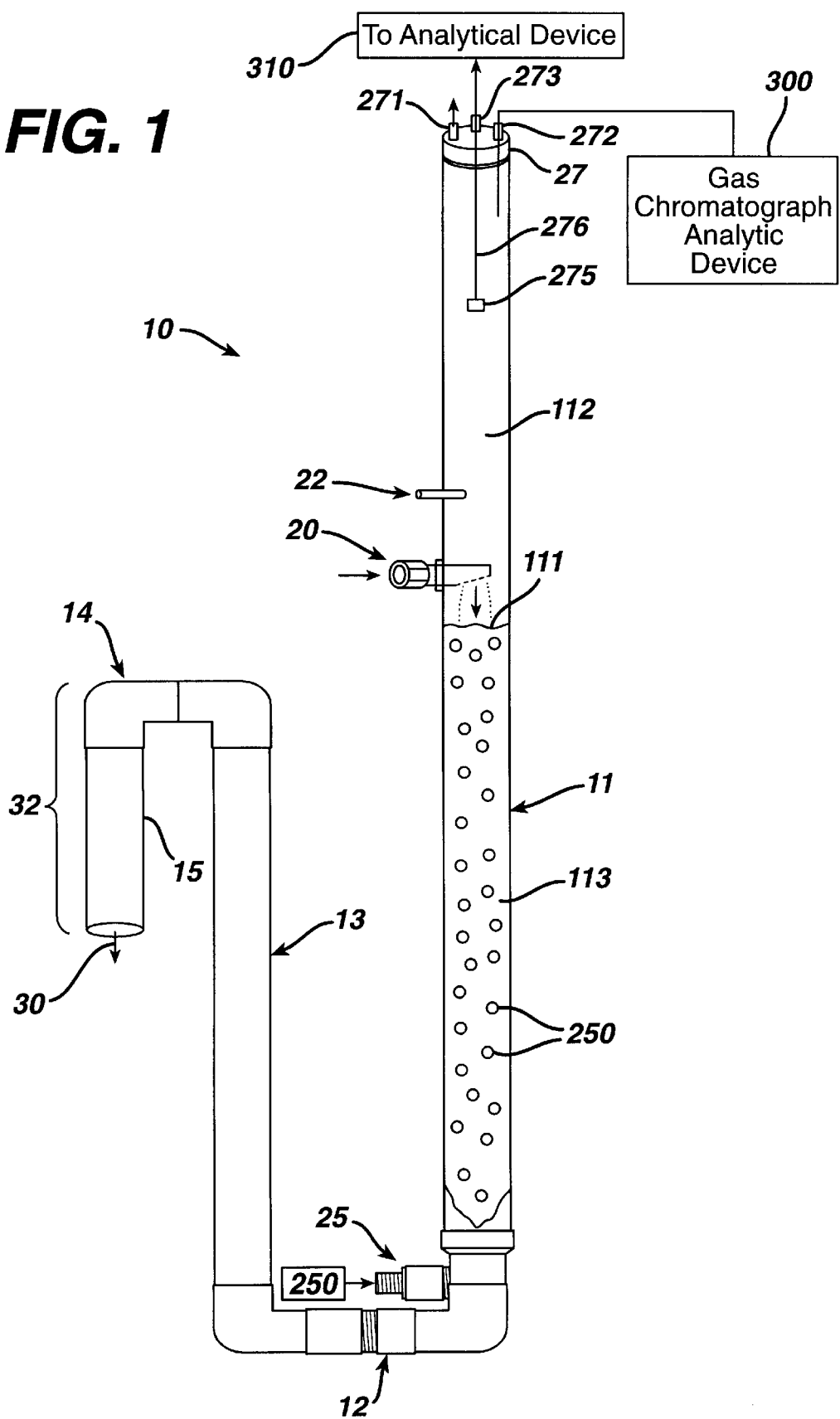
FIG. 1 is a schematic part-sectional illustration of an exemplary on-line sparging sampling and monitoring system, as embodied by the invention.

FIG. 1 is an illustration of an exemplary on-line sparging sampling and monitoring system 10. In FIG. 1, the on-line sparging sampling and monitoring system 10 comprises a network of interconnected tubular members for transporting discharge for monitoring. The on-line sparging sampling and monitoring system 10 comprises a sparger tubular member 11, a bottom connector tubular member 12, a side tubular member 13, a P-trap tubular member 14, and a venting and discharge tubular member 15. The tubular members and connections in the on-line sparging sampling and monitoring system 10 can be configured with dimensions that are sufficient to reduce potential of fouling and blockage by sediments or particulates in aqueous discharge. Thus, filtering of influent aqueous discharge is not needed compared to conventional systems.

The sparger tubular member 11 comprises a cap 27 at one end and is connected to the connecting tubular member 12 at the other end. The cap 27 comprises a plurality of ports for on-line sparging sampling and monitoring system components. The cap 27 comprises a cap exhaust port 271 so that pressure in the sparger tubular member 11 can be connected for be venting to the atmosphere. The cap exhaust port 271 may be vented, connected to an exhaust treatment system, or connected to a condensing system, if desired. The cap 27 also comprises a gas chromatography port 272 that permits gas chromatography of a headspace in the on-line sparging sampling and monitoring system 10, for example micro-gas chromatography (micro-gc) in the sparger tubular member 11. Further, the cap 27 comprises a sensor port 273 that permits a sensor lead 276 that extends from a sensor 275, such as but not limited to, a metal-oxide semiconductor (MOS) sensors and sensor, to pass therealong and connected with analytic devices (as discussed hereinafter).

The sparger tubular member 11 also includes an inlet 20 through which the influent material to be monitored and analyzed is fed. The influent material to be monitored and analyzed often comprises an aqueous discharge, and the remainder of the description of the invention will discuss the material as an aqueous discharge. However, this description is merely exemplary and is not intended to limit the invention in any manner.

The inlet 20 is disposed in the network of tubular members and is positioned in between the cap 27 and a connection of the sparger tubular member 11 to the bottom connector tubular member 12. The inlet 20 and on-line sparging sampling and monitoring system 10 can comprise part of the normal waste and by-product passage for a process being monitored. Alternatively, the inlet 20 and on-line sparging sampling and monitoring system 10 can be connected to the waste and by-product passage by an appropriate fluid connection in which representative samples of the waste and by-products can be drawn into the on-line sparging sampling and monitoring system 10. The influent aqueous discharge establishes an aqueous discharge level 111. A headspace 112 is defined above the aqueous discharge level 111 in which sparged materials, such as VOCs, can be monitored. The aqueous discharge level 111 defines an aqueous discharge portion 113 for sparging, as discussed hereinafter.

Further, the sparger tubular member 11 comprises a gas inlet 22, which is positioned above the inlet 20 so to be disposed between the inlet 20 and the cap 27. The gas inlet 22 permits inert gas, such as, but not limited to, ambient air, to enter the sparger tubular member 11. Thus, the on-line sparging sampling and monitoring system 10 may have equalized pressures during flow without creating back pressures, siphons, vacuums, or the like. The inert gas inlet 22 can be disposed above the aqueous discharge level 111. This positioning facilitates removal of VOCs from the headspace 112. This removal can assist with monitoring in which at least one of process analyzers and sensors can monitor at relatively fast frequencies, such as a frequency in a range between every few seconds to every few minutes, in which a sparging rate is not sufficiently fast to reduce vapor phase sample carryover. The term "carryover" means the transfer of a vapor phase analyte from a sampling event to a subsequent sampling event.

The sparger tubular member 11 also includes a sparger 25, which is disposed close to the connection of the sparger tubular member 11 to the bottom connector tubular member 12. The sparger 25, which will be described in further detail hereinafter with respect to FIG. 2, permits inert non-reactive gas 250 to continuously flow through the aqueous discharge portion 113. The gas introduced into the sparger 25 is inert to avoid any reactions with VOCs and other materials in the aqueous discharge that may adversely influence the analysis. Exemplary gases that can be introduced into the on-line sparging sampling and monitoring system 10 at the sparger 25 include, but are not limited to, air and nitrogen.

The tubular members of the on-line sparging sampling and monitoring system 10 comprise any appropriate material for fluid flow, in which the materials will not be degraded, corroded, or otherwise adversely affected by the aqueous discharge. For example, and in no way limiting of the invention, tubular members for the on-line sparging sampling and monitoring system 10 may comprise polyvinyl chloride (PVC). Other non-reactive inert materials, including thick-walled glass, acrylic, and other clear polymer resins to allow for visual inspection, may also be used for the on-line sparging sampling and monitoring system 10 features. These clear materials allow for visual inspection of the on-line sparging sampling and monitoring system 10.

The on-line sparging sampling and monitoring system 10 may use a single material for the tubular members, and alternatively, the on-line sparging sampling and monitoring system 10 may use a plurality of materials for the tubular members. Further, the tubular members can be connected in any appropriate manner that is sufficient to provide fluid flow therein. For example, and in no way limiting of the invention, each of the tubular members may be threadedly connected to adjacent tubular members. Alternatively, the each of the tubular members may be connected by other connections, such as glued to adjacent tubular members. These types of connections are merely exemplary and are not intended to limit the invention in any manner. The connectors between the tubular members can comprise stainless steel connections, PVC connections, nylon connections, high-density polyethylene (HDPE) connections, and like material.

The features that are connected to the on-line sparging sampling and monitoring system 10, such as, but not limited to, the sparger 25, the inlet 20, the cap 27, and the air inlet 22 may be connected to the on-line sparging sampling and monitoring system 10 by any appropriate manner that is sufficient to provide fluid flow therein. For example, and in no way limiting of the invention, each of the features may be threadedly connected to the respective tubular members. Alternatively, the each of these features may be connected to the respective tubular members by other connections, such as glued to the respective adjacent tubular members. These types of connections are merely exemplary and are not intended to limit the invention in any manner.

The aqueous discharge level in the on-line sparging sampling and monitoring system 10 can controlled at a level by the P-trap tubular member 14 and venting and discharge tubular member 15. The venting and discharge tubular member 15 comprises a vent to the atmosphere, which is generally illustrated as 32, at some point along the on-line sparging sampling and monitoring system 10 above a aqueous discharge flow path through the on-line sparging sampling and monitoring system 10. Thus, the vent 32 can provide atmospheric pressure and relief to the on-line sparging sampling and monitoring system 10 and prevent obstruction of the flow.

The configuration of the vent 32, the venting and discharge tubular member 15, and the on-line sparging sampling and monitoring system 10, allows an aqueous discharge volume 113 (FIG. 1), which is being sparged in the on-line sparging sampling and monitoring system 10, to remain essentially constant. The term "essentially" is used with its conventional meaning in which the volume remains the same mad may undergo minor changes that do not influence the operation or results of the on-line sparging sampling and monitoring system 10. The volume of the aqueous discharge portion 113 can remain essentially constant, even if the influent aqueous discharge flow varies over time. If the aqueous discharge influent flow through the inlet 20 were to stop, the sparging would result in a steady decline in VOCs entering a headspace above the water column.

Figure 2:
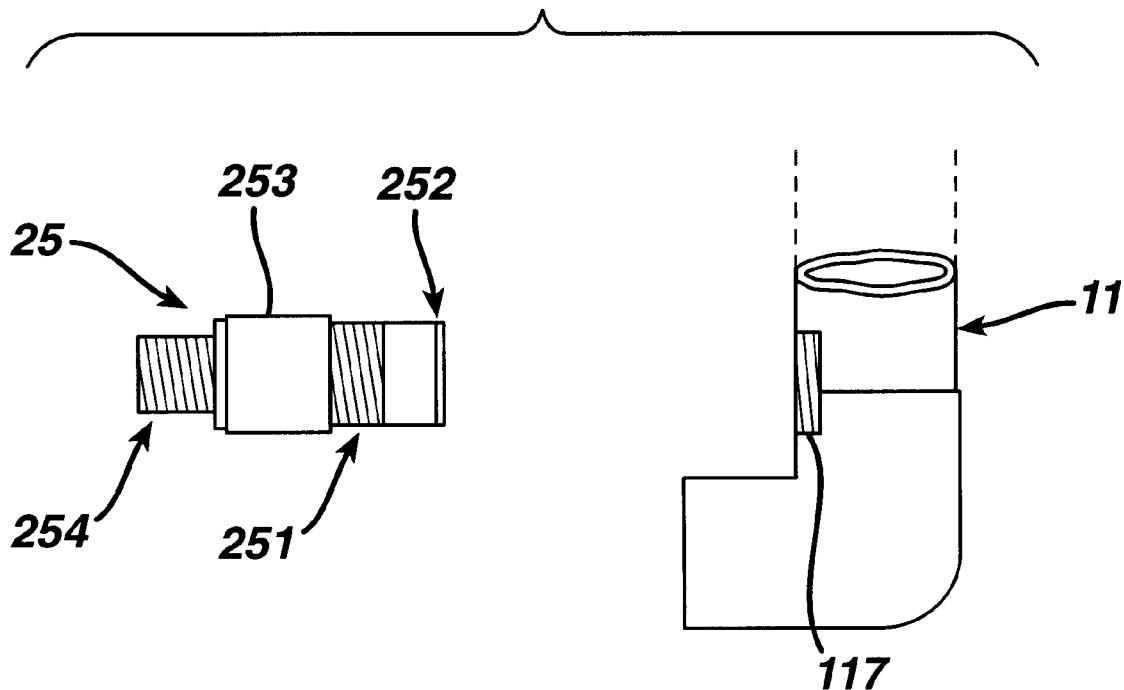
FIG. 2 is a schematic part-sectional illustration of a sparger, as embodied by the invention.

FIG. 2 is an exploded illustration of the sparger 25 for the on-line sparging sampling and monitoring system 10, as embodied by the invention. The sparger 25 is connected to the sparger tubular member 11 at a lower end of the sparger tubular member 11. The connection of the sparger 25 to the sparger tubular member 11 is illustrated with a threaded connection, with threads 251 on the sparger 25 and threads 117 on the sparger tubular member 11. The sparger 25 further comprises a filter disc 252, for example a porous disc with about 2-micron openings therein for the passage of the gas. The diameter of the filter disc 252 is selected to approximately match a diameter of the sparger tubular member 11 and aqueous discharge portion 113 therein. The filter disc 252 is formed of a material selected from stainless steel, glass, polytetrafluoroethylene, and combinations thereof.

The sparger 25 further comprises a body 253 and a further threaded connection 254 that can permit the sparger 25 to be connected to the source of gas for sparging. The connection of the sparger 25 to the sparger tubular member 11 disposes the sparger 25 in a generally parallel configuration to the flow of aqueous discharge. Therefore, the parallel configuration will prevent particulate matter and sediments in the aqueous discharge from depositing on the sparger 25. This parallel configuration can reduce fouling and maintenance of the sparger 25 and on-line sparging sampling and monitoring system 10. The sparger 25 can be easily removed from the sparger tubular member 11 by the threaded connection at 251 and 117 respectively. This threaded connection allows removal, cleaning, and replacement of the sparger 25 if desired.

The sparging rate for the water column is provided at a rate that is sufficient to partition VOC(s) from the aqueous discharge portion 113 to the headspace 112 above the aqueous discharge portion 113. The headspace 112 is closed by the cap 27, which as discussed above, comprises ports through which analytic devices can be coupled to the headspace 112, These analytic devices can comprise, but are not limited to, a gas chromatography device 300, which is illustrated as being connected through port 272, and a sensor 275 based analytic device 310, which extends into the headspace 112 by a lead 276. These ports and devices connected are merely exemplary and are not intended to limit the invention in any manner.

At least a part of the aqueous discharge portion 113 in the sparger tubular member 11 may be heated to facilitate partitioning of VOCs to the headspace 112. Any appropriate device may conduct the heating of the aqueous discharge portion 113. The heating of the aqueous discharge portion 111 can also reduce variations in partitioning efficiencies, for example if there are temperature changes in the environment of the on-line sparging sampling and monitoring system 10.

The analytic devices, 300 and 310, that are connected to the on-line sparging sampling and monitoring system 10 can be selected from a variety of available process analyzers. For example, a MOS sensor 275 and micro-gas chromatography sampler in the on-line sparging sampling and monitoring system 10, when coupled to the headspace portion 112 and connected to the analytic devices, can provide near real-time monitoring and analyzing. The term "real-time" is used with its accepted meaning in the art. For example, the MOS sensor 275 can deliver total hydrocarbon concentration data at response times of about 1 second. Further, micro-micro-gas chromatography systems can provide VOC data at response times of about 6 minutes.

Figure 3:
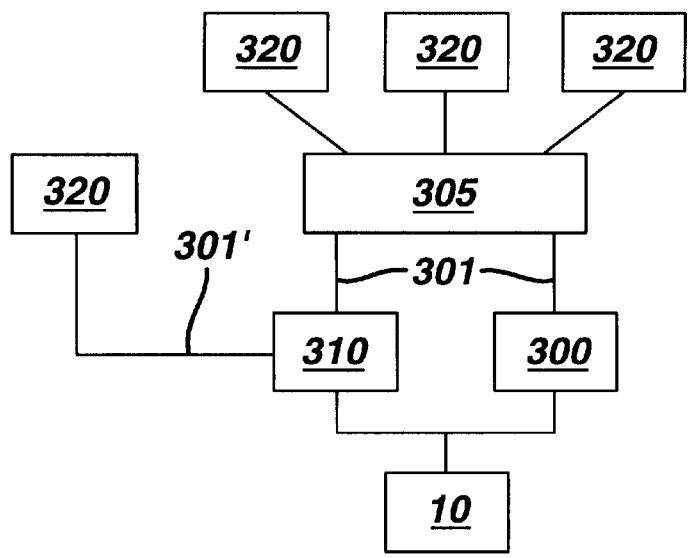
FIG. 3 is a block diagram of a sparging sampling and monitoring system, as embodied by the invention, connected to analytic and communication devices.

The on-line sparging sampling and monitoring system 10 can be connected to communication links for providing the analyzed data to those authorized parties or users of the on-line sparging sampling and monitoring system 10. For example, FIG. 3 illustrates a block diagram of the on-line sparging sampling and monitoring system 10 connected to various users 320 via communication links 301. Further, the information from the analytic devices can be transferred directly to a party, for example by communication link 301'. Alternatively, information from the analytic devices can be transferred directly to a party, for example by communication links 301 that lead to a common data gathering location 305, such as, but not limited to, a web page. The communication links 301 include, but are not limited to include, but are not limited to, at least one of a phone modem, network connection, communication, radio communication and other wireless communication systems, cellular communication, satellite communication, web access communication, and Internet access communication, and combinations thereof.

The use of a web page provides real-time monitoring and analysis data to parties 320 who can readily benefit from the information. In the past, evaluations occurred randomly, irregularly, and may not normally be transmitted in an expedited manner. With the on-line sparging sampling and monitoring system 10, as embodied by the invention, parties that are actually located at the on-line sparging sampling and monitoring system 10 can quickly obtain analyzed and evaluated information, which is provided in a form that is valuable and easy to use. Also, other parties 320 that may not be located at the on-line sparging sampling and monitoring system 10, for example but not limited to regulatory agencies, can also obtain monitored data in real-time, so as to avoid undesirable time delays. With the real-time monitored data, a party 320 may take immediate steps in response to the data. Also, with the real-time monitored. data via the web, feedback from a party can be provided and received via the web.

Figure 4:
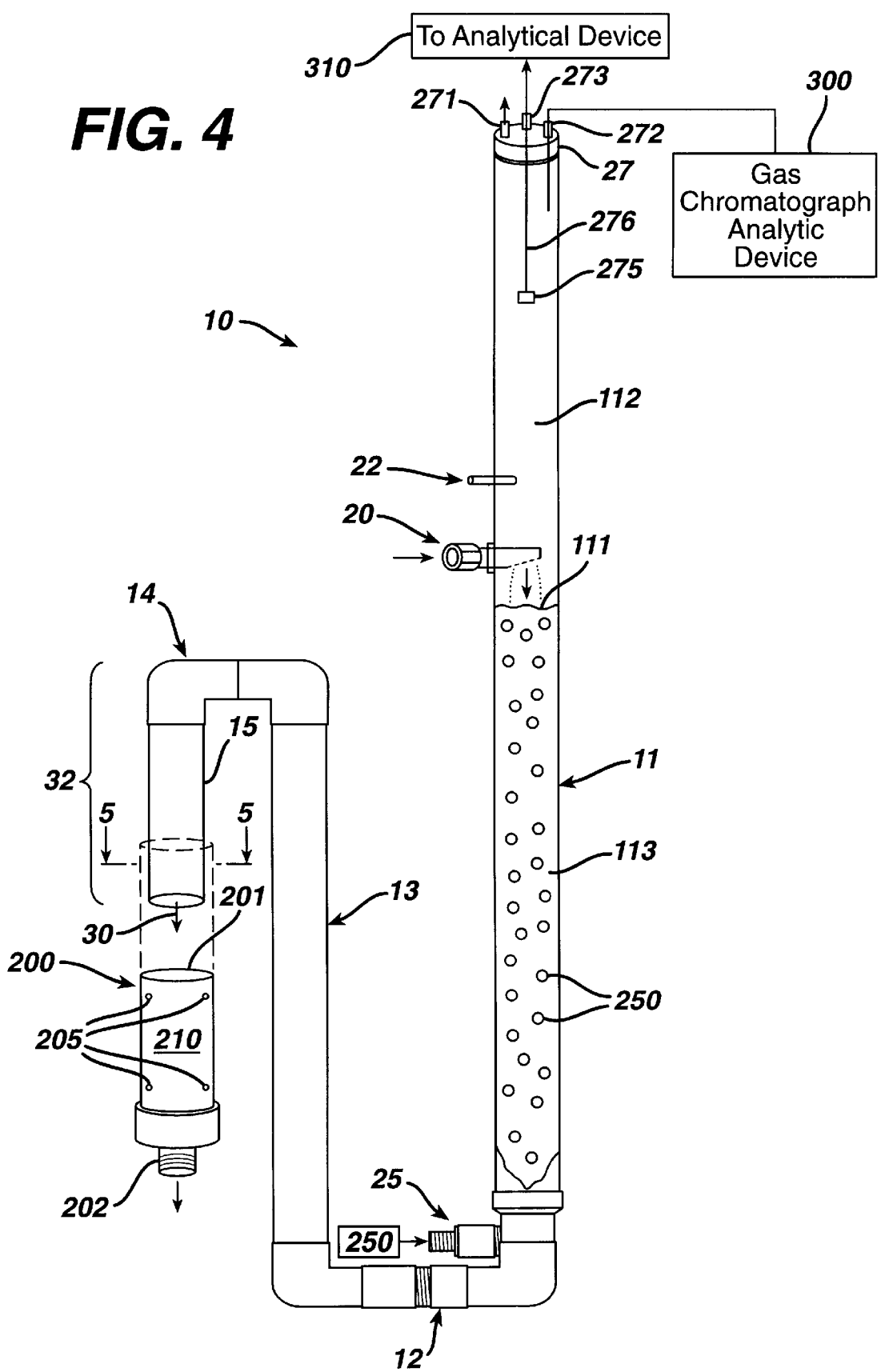
FIG. 4 is a schematic part-sectional illustration of another exemplary on-line sparging sampling and monitoring system, as embodied by the invention.

FIG. 4 illustrates another on-line sparging sampling and monitoring system 10 with a vented waste collector assembly 200. In FIG. 4, features of the on-line sparging sampling and monitoring system 10 as discussed above are provided with like reference numbers. FIG. 4, the vented waste collector assembly 200 is illustrated separated from the venting and discharge tubular member 15, however in operation it is connected thereto (dashed line position). The vented waste collector assembly 200 comprises collector body 210, a vented waste collector inlet 201, an aqueous discharge outlet 202, and at least one spacing arrangement 205. The at least one spacing arrangement 205 positions the vented waste collector assembly 200 on the venting and discharge tubular member 15 in essentially a co-axial relationship. The vented waste collector assembly 200 is provided with an inner diameter d2 that is larger than the outer diameter d1 of the venting and discharge tubular member 15.

Figure 5:
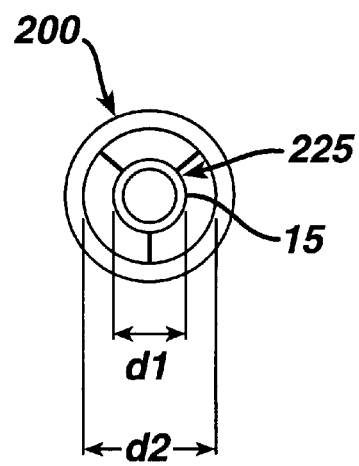
FIG. 5 is a sectional illustration of a vented waste collector assembly for an on-line sparging sampling and monitoring system along line 5—5 of FIG. 4.

FIG. 5 illustrates a coaxial, annular vent space 225 that is defined by the at least one spacing arrangement 205 between the venting and discharge tubular member 15 and the vented waste collector assembly 200. The spacing arrangement 205 separates the vented waste collector assembly 200 from the venting and discharge tubular member 15. Therefore, a generally co-axial vent to the atmosphere is provided in the annular space 225 at a point along the on-line sparging sampling and monitoring system 10. The vent is disposed above an aqueous discharge flow path through the on-line sparging sampling and monitoring system 10. Thus, the vent space can provide atmospheric pressure and relief to the on-line sparging sampling and monitoring system 10 and prevent obstruction of the flow through the on-line sparging sampling and monitoring system 10.

The vented waste collector assembly 200 and the outlet 202 of the vented waste collector assembly 200, as embodied by the invention, be formed of similar material as the tubular members of the on-line sparging sampling and monitoring system 10. The outlet 202 may be provided as a single, integrally formed unit with the vented waste collector assembly 200. Alternatively, the outlet 202 can be provided as a separate component from the vented waste collector assembly 200 and connected thereto by an appropriate connector. The connector for the outlet 202 and the vented waste collector assembly 200 may comprise a connector as described above.

Figure 6:
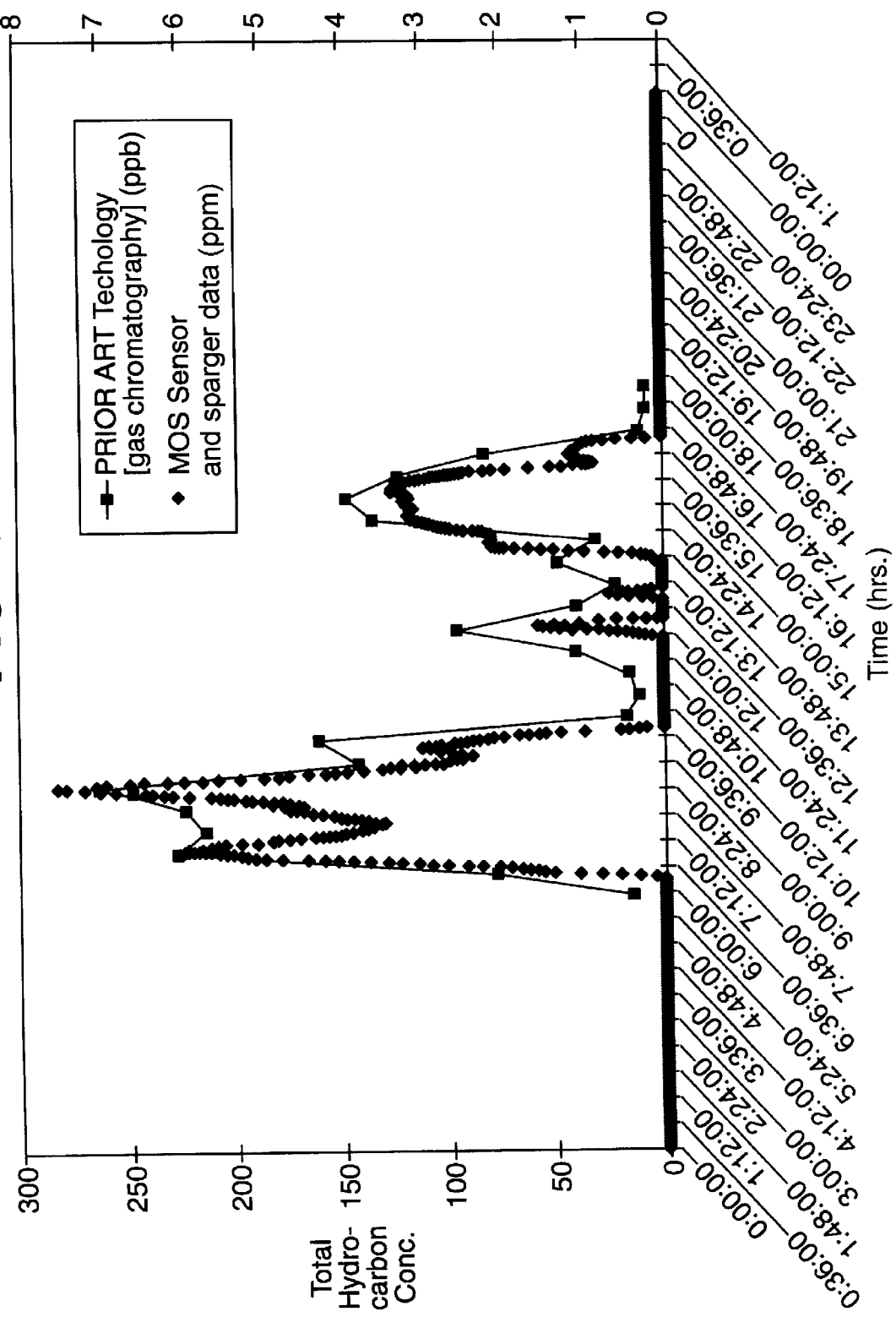
FIG. 6 is a graph of hydrocarbon concentration versus time for monitoring, as embodied by the invention.
Figure 7:
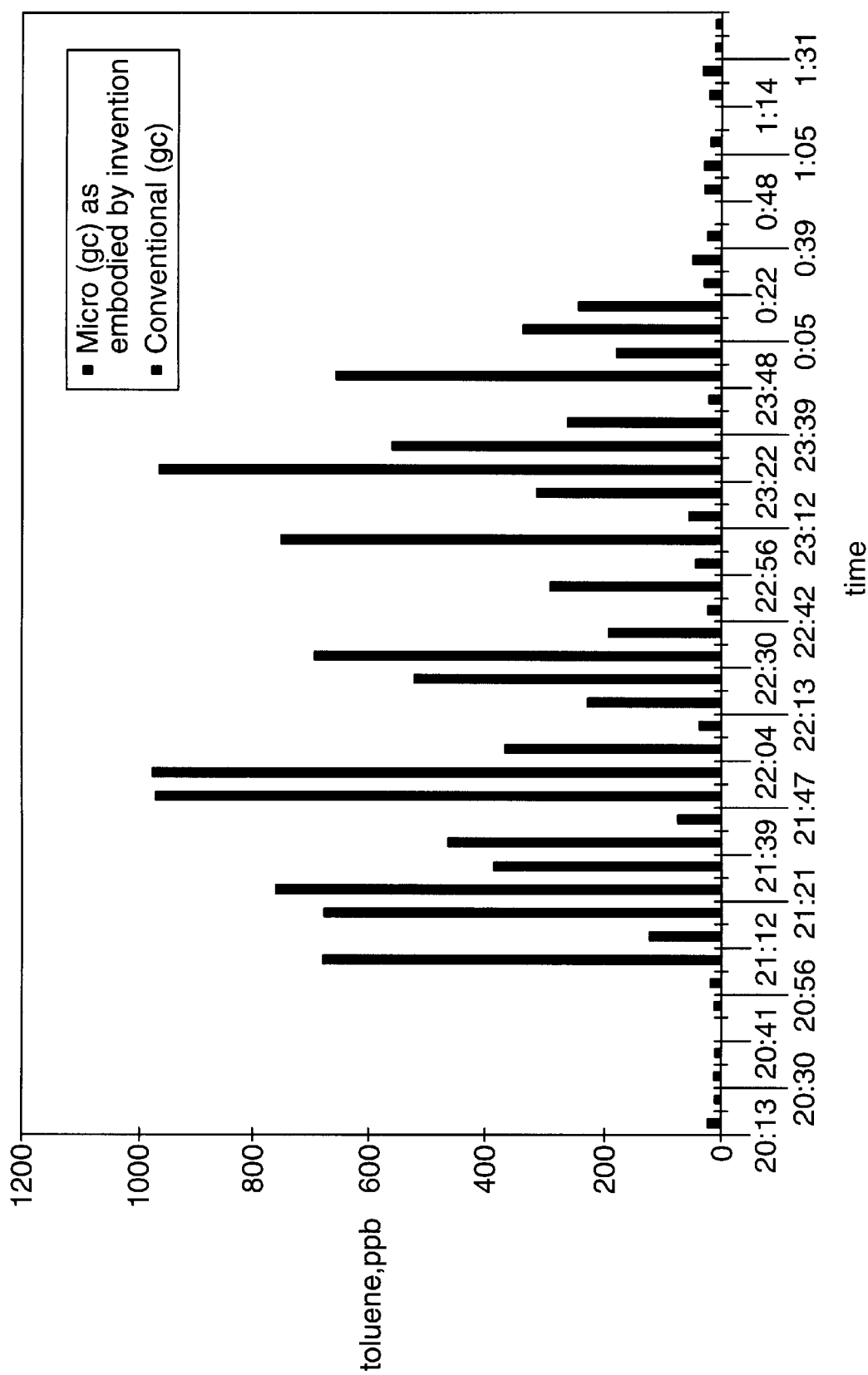
FIG. 7 is a graph of toluene concentration versus time for monitoring, as embodied by the invention.

Exemplary sensor information and data outputs from an on-line sparging sampling and monitoring system 10, as embodied by the invention, are illustrated in FIGS. 6 and 7. FIG. 6 is a graph of hydrocarbon concentration data versus time that has been analyzed by an analytical device connected to a MOS sensor and gas chromatography. FIG. 6 illustrates that the on-line sparging sampling and monitoring system 10 can monitor widely fluctuating VOC concentrations at about 1 minute intervals with a MOS sensor. The graph also illustrates that the data density is improved relative to the gas chromatography process. FIG. 7 is a graph of toluene concentration data versus time that has been analyzed by an analytical device connected to a MOS sensor and gas chromatography. FIG. 7 illustrates similar results with a micro-gas chromatography unit at about 8-minute analysis intervals.

The on-line sparging sampling and monitoring system 10, as embodied by the invention, can provide enhanced monitoring precision for both polar and non-polar hydrocarbons compared to conventional static headspace techniques alone. The on-line sparging sampling and monitoring system 10 provides sampling of both non-polar and polar VOCs together without separate monitoring setups. Further, the on-line sparging sampling and monitoring system 10 can be configured for real-time monitoring and can be coupled to continuous or automated process analyzers. Thus, the on-line sparging sampling and monitoring system 10 can provide real-time data for process control and feedback, without time delays experienced by conventional sampling and monitoring systems.

Further, the design of the on-line sparging sampling and monitoring system 10 can be scaled to accommodate a wide range of influent flow rates. The tubular members and connections of the on-line sparging sampling and monitoring system 10 can be configured with dimensions that are sufficient to reduce fouling and blockage by sediments or particulates. Thus, filtering of influent aqueous discharge is avoided. The on-line sparging sampling and monitoring system 10 also provides for an essentially constant volume of aqueous discharge portion 113, in which the P-trap tubular member 115 can assist in maintaining a volume in the on-line sparging sampling and monitoring system 10 essentially constant. Therefore, influent aqueous discharge variations do not adversely influence the on-line sparging sampling and monitoring system 10.

While various embodiments are described herein, it will be appreciated from the specification that various combinations of elements, variations or improvements therein may be made by those skilled in the art, and are within the scope of the invention.

We claim:

1. An on-line sparging sampling system for sparging polar and non-polar volatile organic compounds from aqueous discharge, the system comprising:

a network of tubular members that are connected to each other to define a fluid passage, the network of tubular members comprising an inlet for influent aqueous discharge into the network of tubular members and an outlet comprising a venting and discharge tubular member for the discharge of aqueous discharge from the on-line sparging sampling and monitoring system, wherein the network of interconnected tubular members comprise at least a vertically extending sparger tubular member having an inlet, the sparger tubular member being connected at its lower end to a horizontally extending bottom connector tubular member, which is connected to a vertically extending side tubular member, which is connected at its top end to a P-trap tubular member, which is connected to said venting and discharge tubular member;

a sparger disposed in the network of tubular members, the sparger being disposed between the inlet and the outlet of the aqueous discharge so that aqueous discharge flows by the sparger, the sparger providing inert non-reactive gas to the on-line sparging sampling and monitoring system; and at least one analytic device connected to the on-line sparging sampling and monitoring system for analyzing volatile organic compounds in the aqueous discharge;

wherein the aqueous discharge forms an aqueous discharge portion and a headspace during flow through the network of tubular members, the sparger providing the inert non-reactive gas to flow through the aqueous discharge portion, the inert non-reactive gas partitioning volatile organic compounds from the aqueous discharge portion to the headspace so that polar and nonpolar volatile organic compounds can be analyzed by the at least one analytic device.

2. A system according to claim 1, wherein the sparger is disposed in the sparger tubular member proximate to the bottom connector tubular member, which is connected to a side tubular member.

3. A system according to claim 2, wherein the sparger is disposed essentially in parallel with a flow of aqueous discharge in the on-line sparging sampling and monitoring system.

4. A system according to claim 2, wherein the network of tubular members comprise non-reactive inert materials.

5. A system according to claim 4, wherein the non-reactive inert materials are selected from at least one of polyvinyl chloride, glass, acrylic, and polymer resins.

6. A system according to claim 2, wherein the network of tubular members is connected by connections selected from threaded connections, glued connections.

7. A system according to claim 6, wherein each connection comprises at least one of stainless steel, PVC, nylon, and high-density polyethylene (HDPE).

8. A system according to claim 2, wherein the network of tubular members comprise a size sufficient to remain open with a flow of particulate and sediment ladened aqueous discharge.

9. A system according to claim 2, wherein the venting and discharge tubular member comprises the outlet.

10. A system according to claim 2, wherein the venting and discharge tubular member comprises a vent, the vent providing atmospheric pressure to the on-line sparging sampling and monitoring system to prevent flow stoppage.

11. A system according to claim 2, wherein the sparger tubular member comprises a gas inlet for adding inert gas to the on-line sparging sampling and monitoring system, the inert gas inlet being disposed in the headspace and providing sufficient pressure to essentially equalize pressure in the on-line sparging sampling and monitoring system during flow.

12. A system according to claim 2, wherein the sparger tubular member comprises a cap on one end proximate the headspace, the at least one analytic device communicating with the headspace through the cap.

13. A system according to claim 12, wherein the cap comprises at least one port that allows communication of the at least one analytic device with the headspace.

14. A system according to claim 12, wherein the at least one analytic device comprises at least one of a gas chromatography device and a MOS sensor analytic device, and the cap comprises individual ports for each analytic device.

15. A system according to claim 12, wherein the cap comprises an exhaust vent port that allows gases in the headspace to be exhausted.

16. A system according to claim 15, wherein the exhaust vent port communicates gases in the headspace to at least one of the atmosphere, a condenser, and an exhaust gas treatment system.

17. A system according to claim 1, wherein the at least one analytic device comprises at least one of a gas chromatography device and a MOS sensor analytic device.

18. A system according to claim 1, wherein the sparger comprises a threaded connection to the network of tubular members, the sparger being disposed in an essentially parallel orientation to the flow in the network of tubular members.

19. A system according to claim 1, wherein the sparger comprises a filter disc for passing gas into the aqueous discharge, in which the gas comprises an inert gas for sparging volatile organic compounds from the aqueous discharge to the headspace.

20. A system according to claim 19, wherein the disc comprises at least one of stainless steel, glass, polytetrafluoroethylene, and combinations thereof.

21. A system according to claim 1, wherein the outlet comprises a vented waste collector assembly, the vented waste collector assembly comprising a vent assembly for venting the on-line sparging sampling and monitoring system and the outlet.

22. A system according to claim 21, wherein the vented waste collector assembly comprises a collector body, a collector inlet, an outlet, and at least one spacing arrangement for spacing the vented waste collector assembly from the network of tubular members.

23. A system according to claim 22, wherein the spacing arrangement co-axially disposes the collector body on the network of tubular members to define a annular vent space between the vented waste collector assembly and the network of tubular members.

24. A system according to claim 1, further comprising at least one communication link that connects the on-line sparging sampling and monitoring system to at least one party, wherein the communication link comprises at least one of a phone modem, network connection, communication, radio communication and other wireless communication systems, cellular communication, satellite communication, web access communication, and Internet access communication, and combinations thereof.

25. A system according to claim 1, further comprising at least one communication link that connects the on-line sparging sampling and monitoring system to at least one party, wherein the communication link comprises Internet access communication.

26. A system according to claim 1, wherein further comprising at least one communication link that connects the on-line sparging sampling and monitoring system to provide real-time data to at least one party.

27. A method for on-line sparge sampling by sparging polar and non-polar volatile organic compounds from aqueous discharge using an on-line sparging sampling and monitoring system, the method comprising:

providing a network of tubular members that are interconnected to each other to define a fluid passage, wherein the network of interconnected tubular members comprise at least a vertically extending sparger tubular member having an inlet, the sparger tubular member being connected at its lower end to a horizontally extending bottom connector tubular member, which is connected to a vertically extending side tubular member, which is connected at its top end to a P-trap tubular member, which is connected to a venting and discharge tubular member;

providing an inlet for influent aqueous discharge into the network of tubular members and an outlet for discharge from the on-line sparging sampling and monitoring system;

disposing a sparger between the inlet and the outlet comprising said venting and discharge tubular member for the aqueous discharge;

flowing aqueous discharge by the sparger;

providing inert non-reactive gas from the sparger to flow through the aqueous discharge in the on-line sparging sampling and monitoring system;

flowing the inert gas through the aqueous discharge;

forming an aqueous discharge portion and a headspace in the network of tubular members during aqueous discharge flow through the network of tubular members;

monitoring and analyzing the sparged aqueous discharge in the on-line sparging sampling and monitoring system for volatile organic compounds using at least one analytic device; and partitioning volatile organic compounds from the aqueous discharge portion to the headspace so that polar and non-polar volatile organic compounds can be analyzed.

28. A method according to claim 27, wherein the step of disposing the sparger comprises disposing the sparger tubular member proximate to the bottom connector tubular member, which is connected to a side tubular member.

29. A method according to claim 28, wherein the step of disposing the sparger comprises disposing the sparger essentially in parallel with an aqueous discharge flow in the on-line sparging sampling and monitoring system.

30. A method according to claim 29, wherein the network of tubular members comprises a non-reactive inert material.

31. A method according to claim 30, wherein the non-reactive inert material is selected from polyvinyl chloride, glass, acrylic, and polymer resins.

32. A method according to claim 29, wherein the step of providing a network of tubular members comprises connecting the network of tubular members by a connection selected from threaded connections and glued connections.

33. A method according to claim 32, wherein each connection comprises at least one of stainless steel, PVC, nylon, and high-density polyethylene (HDPE).

34. A method according to claim 29, wherein the step of providing the network of tubular members comprises forming each tubular member with a size sufficient to remain open with a flow of particulate and sediment ladened aqueous discharge.

35. A method according to claim 29, wherein the venting and discharge tubular member comprises the outlet.

36. A method according to claim 29, wherein the venting and discharge tubular member comprises a vent, the vent providing atmospheric pressure to the on-line sparging sampling and monitoring system to prevent aqueous discharge flow stoppage.

37. A method according to claim 29, wherein the sparger tubular member comprises a gas inlet for adding inert gas to the on-line sparging sampling and monitoring system, the method comprising adding the inert gas inlet in the headspace and for essentially equalizing pressures during aqueous discharge flow.

38. A method according to claim 29, wherein the step of providing a network of tubular members comprises providing a sparger tubular member having a cap on one end proximate the headspace, the at least one analytic device communicating with the headspace through the cap.

39. A method according to claim 38, wherein the cap comprises at least one port that allows communication of the at least one analytic device with the headspace.

40. A method according to claim 39, wherein the analytic device comprises at least on of a gas chromatography device and a MOS sensor analytic device, and the cap comprises individual ports for each analytic device.

41. A method according to claim 39, wherein the cap comprises an exhaust vent port that allows gases in the headspace to be exhausted.

42. A method according to claim 39, wherein the exhaust port communicates gases in the headspace to at least one of the atmosphere, a condenser, and an exhaust gas treatment system.

43. A method according to claim 39, wherein the analytic device comprises at least one of a gas chromatography device and a MOS sensor analytic device.

44. A method according to claim 29, wherein the step of disposing a sparger comprises threadingly connecting the sparger to the network of tubular members, and disposing the sparger in an essentially parallel orientation to the aqueous discharge flow.

45. A method according to claim 29, wherein the sparger comprises a filter disc for passing gas into the aqueous discharge in the on-line sparging sampling and monitoring system, in which the gas comprises an inert gas for sparging volatile organic compounds.

46. A method according to claim 45, wherein the disc comprises at least one of stainless steel, glass, polytetrafluoroethylene, and combinations thereof.

47. A method according to claim 29, wherein the outlet comprises a vented waste collector assembly, the vented waste collector assembly comprising a vent assembly for venting the on-line sparging sampling and monitoring system and the outlet.

48. A method according to claim 29, wherein the step of providing a network of tubular members comprises providing a vented waste collector assembly comprising a collector body, a collector inlet, an outlet, and at least one spacing arrangement for spacing the vented waste collector assembly from the network of tubular members.

49. A method according to claim 48, wherein the spacing arrangement co-axially disposes the collector body on the network of tubular members to define an annular vent space between the vented waste collector assembly and the network of tubular members.

50. A method according to claim 27, the method further comprising providing at least one communication link for connecting the on-line sparging sampling and monitoring system to at least one party, wherein the communication link comprises at least one of a phone modem, network connection, communication, radio communication and other wireless communication systems, cellular communication, satellite communication, web access communication, and Internet access communication, and combinations thereof.

51. A method according to claim 27, the method further comprising providing at least one communication link that connects the on-line sparging sampling and monitoring system to at least one party, wherein the communication link comprises Internet access communication.

52. A method according to claim 27, the method further comprising providing at least one communication link that connects the on-line sparging sampling and monitoring system to provide real-time data to at least one party.

* * * * *